United States Patent
Shriver et al.

(10) Patent No.: US 9,638,678 B2
(45) Date of Patent: May 2, 2017

(54) SYSTEM AND METHOD FOR CROP HEALTH MONITORING

(71) Applicant: AgriSight, Inc., Ann Arbor, MI (US)

(72) Inventors: John Shriver, Ann Arbor, MI (US); Mayank Agarwal, Ann Arbor, MI (US)

(73) Assignee: AgriSight, Inc., Ann Arbor, MI (US)

( * ) Notice: Subject to any disclaimer, the term of this patent is extended or adjusted under 35 U.S.C. 154(b) by 0 days.

(21) Appl. No.: 15/012,738

(22) Filed: Feb. 1, 2016

(65) Prior Publication Data

US 2016/0223506 A1 Aug. 4, 2016

Related U.S. Application Data

(60) Provisional application No. 62/109,834, filed on Jan. 30, 2015, provisional application No. 62/173,169, filed on Jun. 9, 2015.

(51) Int. Cl.
| | |
|---|---|
| *G06K 9/00* | (2006.01) |
| *G01N 33/00* | (2006.01) |
| *G06Q 50/02* | (2012.01) |
| *G06T 7/00* | (2017.01) |
| *G06T 11/00* | (2006.01) |

(52) U.S. Cl.
CPC ......... *G01N 33/0098* (2013.01); *G06Q 50/02* (2013.01); *G06T 7/001* (2013.01); *G06T 11/001* (2013.01); *G06T 2207/30128* (2013.01); *G06T 2207/30188* (2013.01)

(58) Field of Classification Search
None
See application file for complete search history.

(56) References Cited

U.S. PATENT DOCUMENTS

| | | | |
|---|---|---|---|
| 5,497,419 A | 3/1996 | Hill | |
| 6,525,276 B1 * | 2/2003 | Vellidus | A01B 79/005 177/136 |
| 6,751,515 B2 | 6/2004 | Moore | |
| 7,031,927 B1 | 4/2006 | Beck et al. | |
| 7,058,197 B1 * | 6/2006 | McGuire | G06K 9/00657 382/100 |
| 7,068,816 B1 * | 6/2006 | Knoblauch | A01B 79/005 348/144 |
| 9,113,590 B2 * | 8/2015 | Johnson | A01B 79/005 |

(Continued)

FOREIGN PATENT DOCUMENTS

WO 2014120887 A1 8/2014

*Primary Examiner* — Iman K Kholdebarin
(74) *Attorney, Agent, or Firm* — Jeffrey Schox; Diana Lin

(57) ABSTRACT

A method for monitoring crop health of a geographic region includes receiving an image comprising a set of image elements, the image corresponding to a time unit, mapping an image element of the set of image elements to a geographic sub-region of the geographic region, determining a geographic region performance value for the image element, determining a geographic region performance value change, and identifying a crop health anomaly based on the geographic region performance change and an expected geographic region performance value change. Determining the geographic region performance value for the image element can include determining a vegetative performance value for the image element, mapping the image element to a crop type, and normalizing the vegetative performance value.

20 Claims, 6 Drawing Sheets

(56) References Cited

U.S. PATENT DOCUMENTS

| | | | |
|---|---|---|---|
| 9,131,644 B2* | 9/2015 | Osborne | A01G 7/00 |
| 2002/0091458 A1* | 7/2002 | Moore | A01D 41/127 |
| | | | 700/110 |
| 2003/0028321 A1 | 2/2003 | Upadhyaya et al. | |
| 2004/0077347 A1 | 4/2004 | Lauber et al. | |
| 2004/0194442 A1 | 10/2004 | Maertens | |
| 2005/0108100 A1 | 5/2005 | Veen et al. | |
| 2006/0017551 A1 | 1/2006 | Neher et al. | |
| 2007/0038338 A1* | 2/2007 | Larschan | G07C 5/008 |
| | | | 701/2 |
| 2007/0065857 A1* | 3/2007 | Glaser | G01N 21/314 |
| | | | 435/6.11 |
| 2008/0195268 A1 | 8/2008 | Sapilewski et al. | |
| 2008/0304711 A1* | 12/2008 | Scharf | A01C 21/007 |
| | | | 382/110 |
| 2010/0069035 A1* | 3/2010 | Johnson | H04W 4/02 |
| | | | 455/404.1 |
| 2011/0270723 A1* | 11/2011 | O'Neil | G06Q 10/06 |
| | | | 705/34 |
| 2011/0270724 A1* | 11/2011 | O'Neil | G06Q 10/087 |
| | | | 705/34 |
| 2011/0290873 A1* | 12/2011 | Nishiguchi | A01B 79/005 |
| | | | 235/376 |
| 2012/0101784 A1* | 4/2012 | Lindores | G01D 18/00 |
| | | | 703/2 |
| 2012/0123817 A1* | 5/2012 | Hohenberger | G06Q 10/0631 |
| | | | 705/7.12 |
| 2012/0237083 A1* | 9/2012 | Lange | G06K 9/00805 |
| | | | 382/103 |
| 2012/0280797 A1* | 11/2012 | Meyers | G06Q 10/087 |
| | | | 340/10.5 |
| 2013/0226607 A1* | 8/2013 | Woody | G06Q 10/063114 |
| | | | 705/2 |
| 2014/0012732 A1* | 1/2014 | Lindores | A01B 79/005 |
| | | | 705/37 |
| 2014/0205154 A1* | 7/2014 | De Souza | G06K 9/00657 |
| | | | 382/110 |
| 2014/0278645 A1 | 9/2014 | Davidson et al. | |
| 2015/0278640 A1* | 10/2015 | Johnson | G06T 7/408 |
| | | | 382/110 |
| 2015/0278838 A1* | 10/2015 | Rasa | G06Q 30/0205 |
| | | | 705/7.34 |
| 2015/0278966 A1* | 10/2015 | Johnson | G06Q 10/063 |
| | | | 702/2 |
| 2016/0042232 A1* | 2/2016 | Scharf | G06Q 10/06315 |
| | | | 382/110 |
| 2016/0078375 A1* | 3/2016 | Ethington | G06Q 10/0633 |
| | | | 705/7.27 |
| 2016/0078570 A1* | 3/2016 | Ethington | G06Q 10/1097 |
| | | | 705/7.21 |
| 2016/0112362 A1 | 4/2016 | Perazzo et al. | |

* cited by examiner

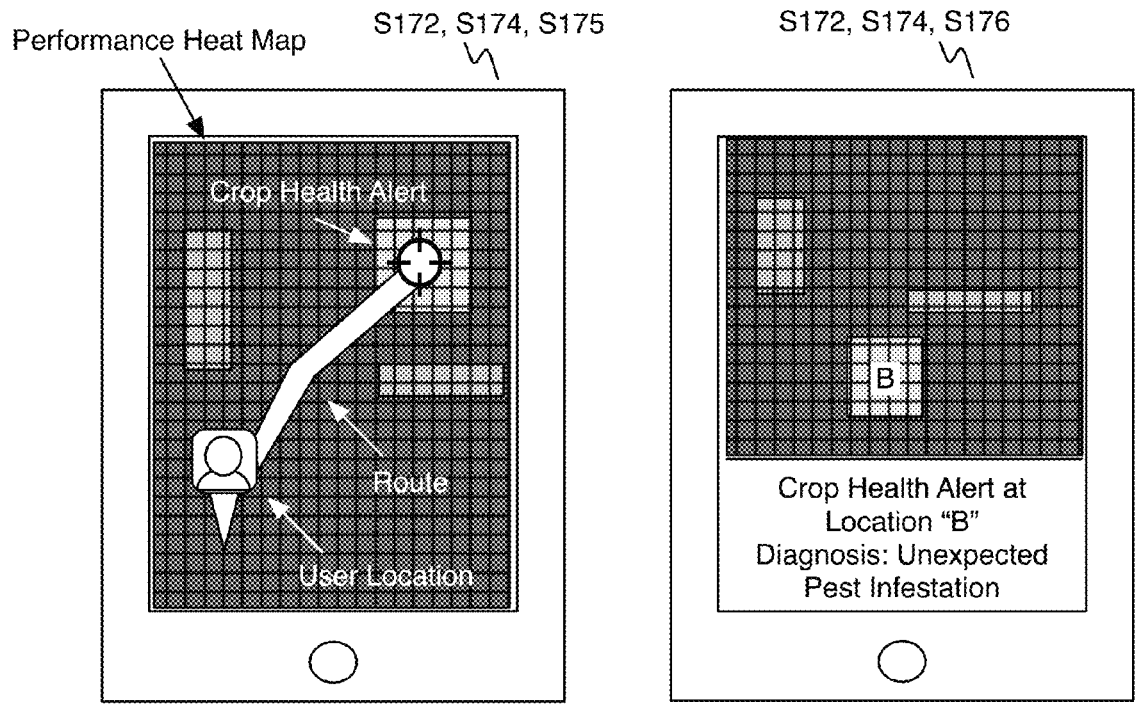
FIGURE 7A
FIGURE 7B
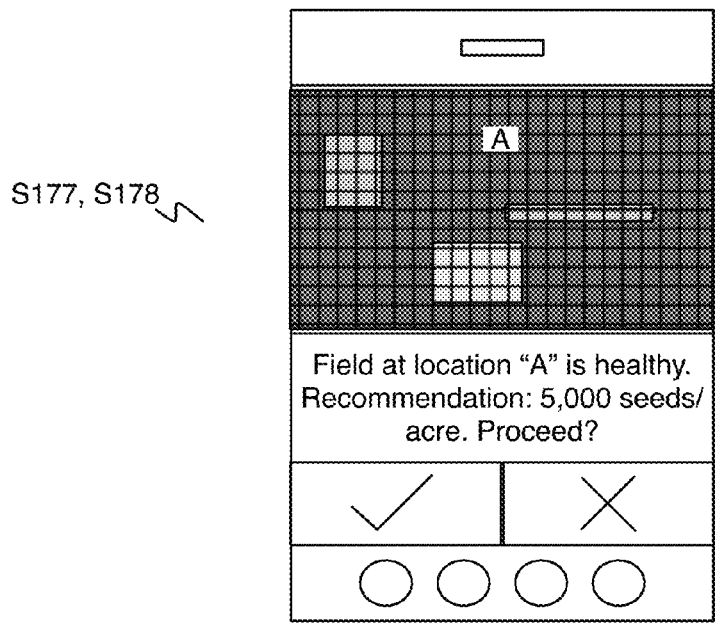
FIGURE 7C

SYSTEM AND METHOD FOR CROP HEALTH MONITORING

CROSS-REFERENCE TO RELATED APPLICATIONS

This application claims the benefit of U.S. Provisional Application Ser. No. 62/109,834, filed on 30 Jan. 2015, and U.S. Provisional Application Ser. No. 62/173,169, filed on 9 Jun. 2015, which are incorporated herein in their entireties by this reference.

This application is related to U.S. application Ser. No. 15/012,762, titled "System and Method for Field Variance Determination" filed on 10 Feb. 2016, which claims the benefit of U.S. Provisional Application No. 62/109,888 filed 30 Jan. 2015 and U.S. Provisional Application No. 62/130,314 filed 9 Mar. 2015, all of which are incorporated herein in their entireties by this reference.

TECHNICAL FIELD

This invention relates generally to the agricultural field, and more specifically to a new and useful system and method for crop monitoring in the agricultural field.

BRIEF DESCRIPTION OF THE FIGURES

FIGS. 7A-7C are graphical representations of notifying a user.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
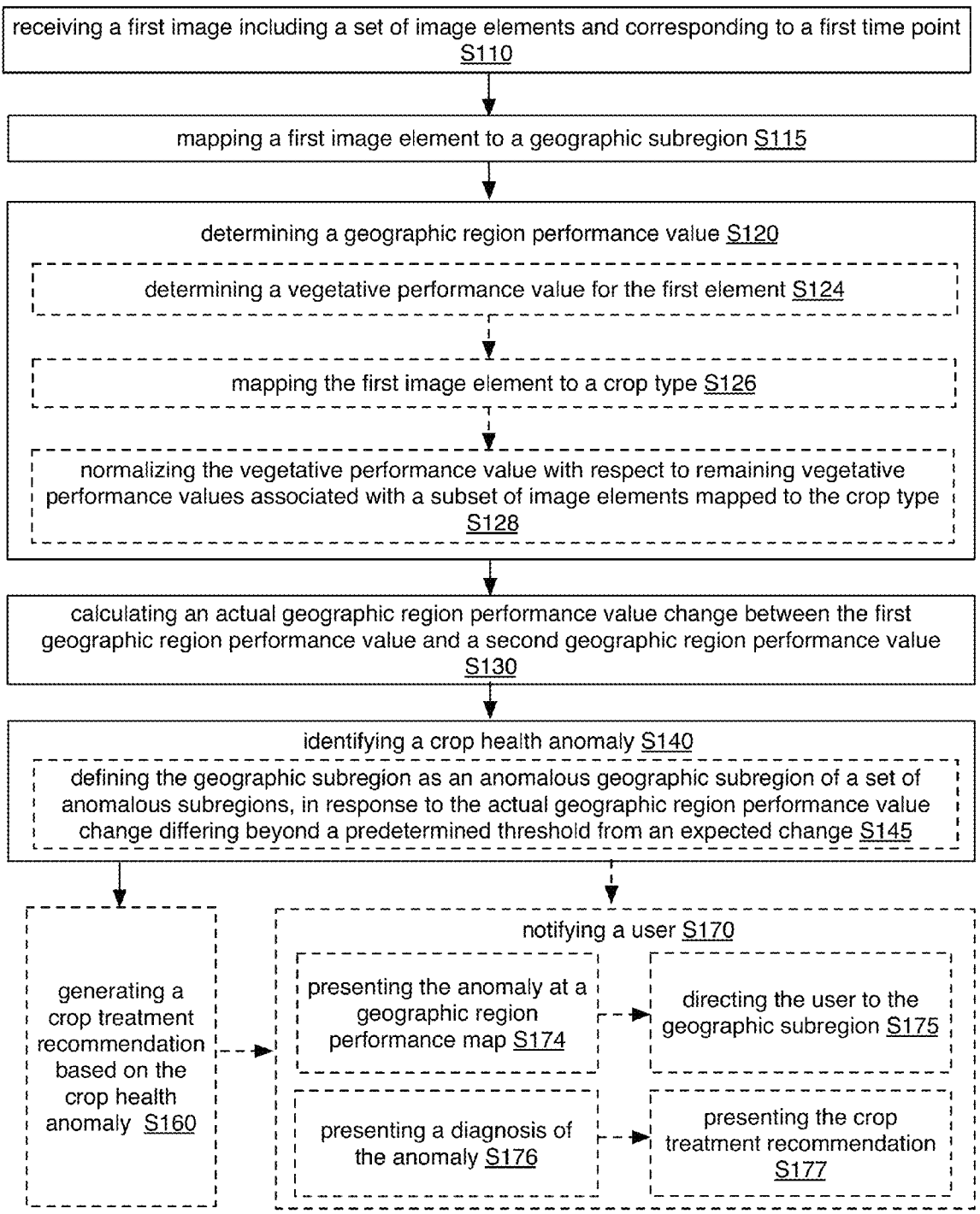
FIG. 1 is a flowchart representation of the method for crop health monitoring.
Figure 2:
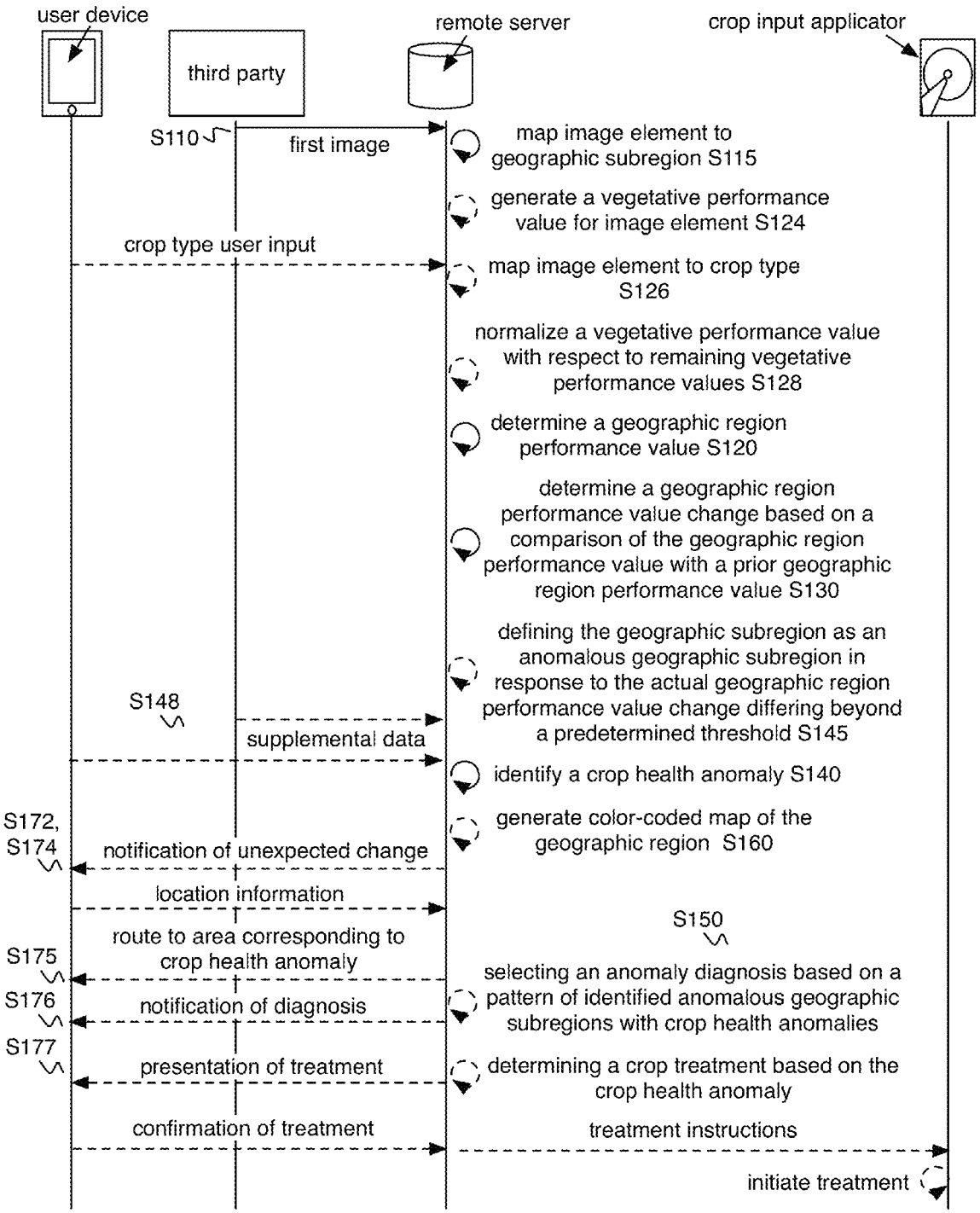
FIG. 2 is a flowchart representation of the method for crop health monitoring.

As shown in FIGS. 1-2, a method 100 for monitoring crop health of a geographic region includes receiving an image including a set of image elements, the image corresponding to a time unit S110, mapping an image element of the set of image elements to a geographic sub-region of the geographic region S115, determining a geographic region performance value for the image element S120, and identifying a crop health anomaly based on the geographic region performance value and an expected geographic region performance value S140.

Determining the geographic region performance value for the image element S120 can additionally or alternatively include determining a vegetative performance value for the image element S124, mapping the image element to a crop type S126, and/or normalizing the vegetative performance value S128. Identifying a crop health anomaly S140 can additionally or alternatively include defining the geographic sub-region as an anomalous geographic sub-region S145. Identifying a crop health anomaly can additionally or alternatively include determining a geographic region performance value change S130, and identifying the crop health anomaly based on the geographic region performance value change and an expected geographic region performance value change. The method 100 can additionally or alternatively include diagnosing the crop health anomaly S150, determining a crop treatment S160, and/or notifying a user S170.

The method 100 functions to identify crop field regions that are affected by plant diseases, pathogens, injuries, stressors, benefactors, or any other suitable desirable or undesirable effect on the crops. Parameters of the identified anomalous region (e.g., the shape, change in severity over time, etc.) can additionally be used to identify the underlying cause of the anomaly (e.g., diseases, pathogens, injuries, stressors, etc.) and/or to recommend or initiate treatment on the affected area.

The method 100 preferably functions to remotely monitor a geographic region (e.g., a crop field) for unexpected crop health anomalies. The method can further function to classify the crop anomaly and prescribe a treatment to rectify the crop anomaly. In this variation, the method 100 can leverage a set of historical baselines (e.g., expected change) for the geographic region for each of a set of recurring time units (e.g., calendar months). In one example, each historical baseline includes an expected performance percentile for each geographic sub-region within a geographic region.

Figure 3:
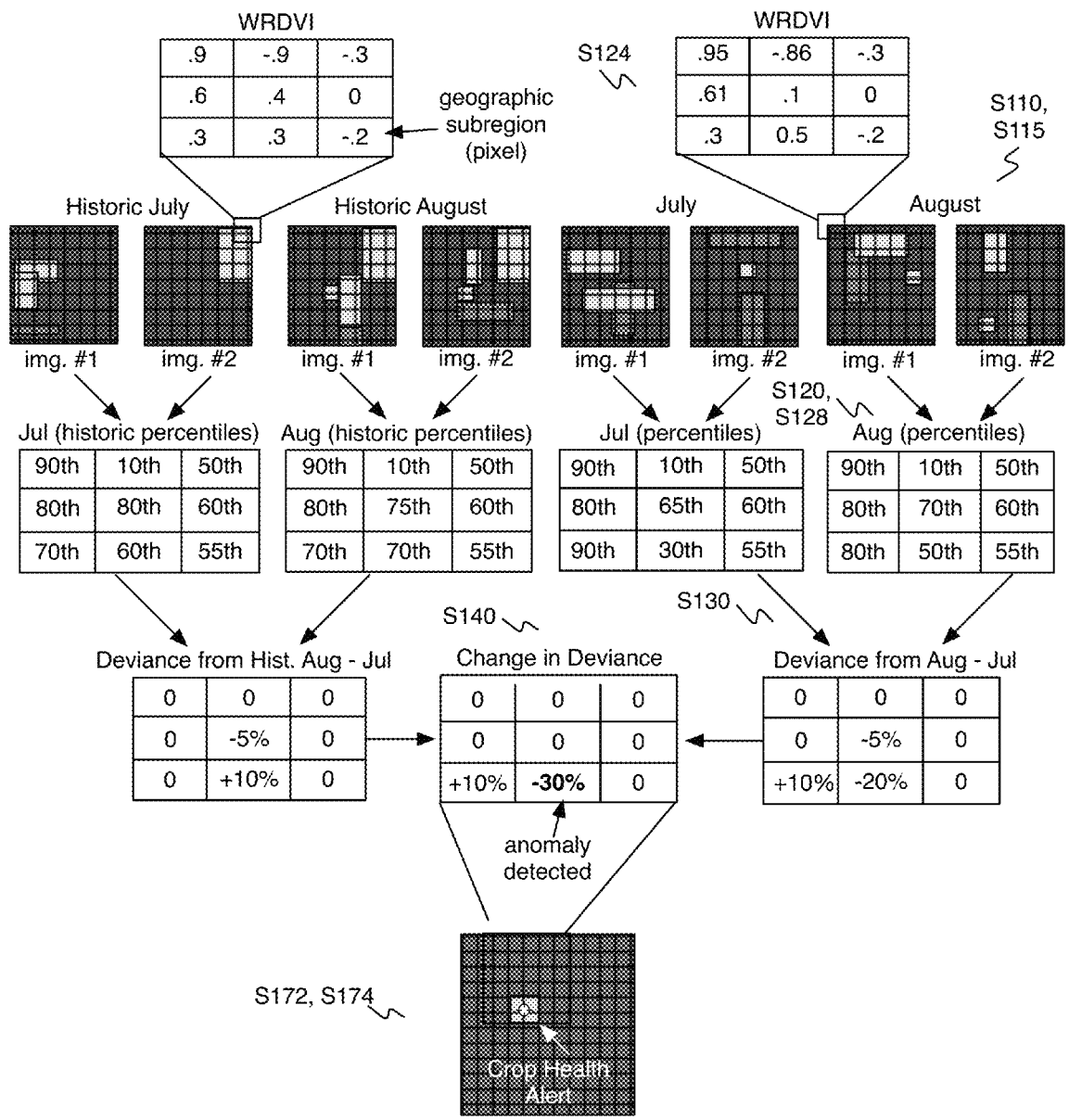
FIG. 3 is a schematic representation of the method for anomaly detection in crop health monitoring.
Figure 4:
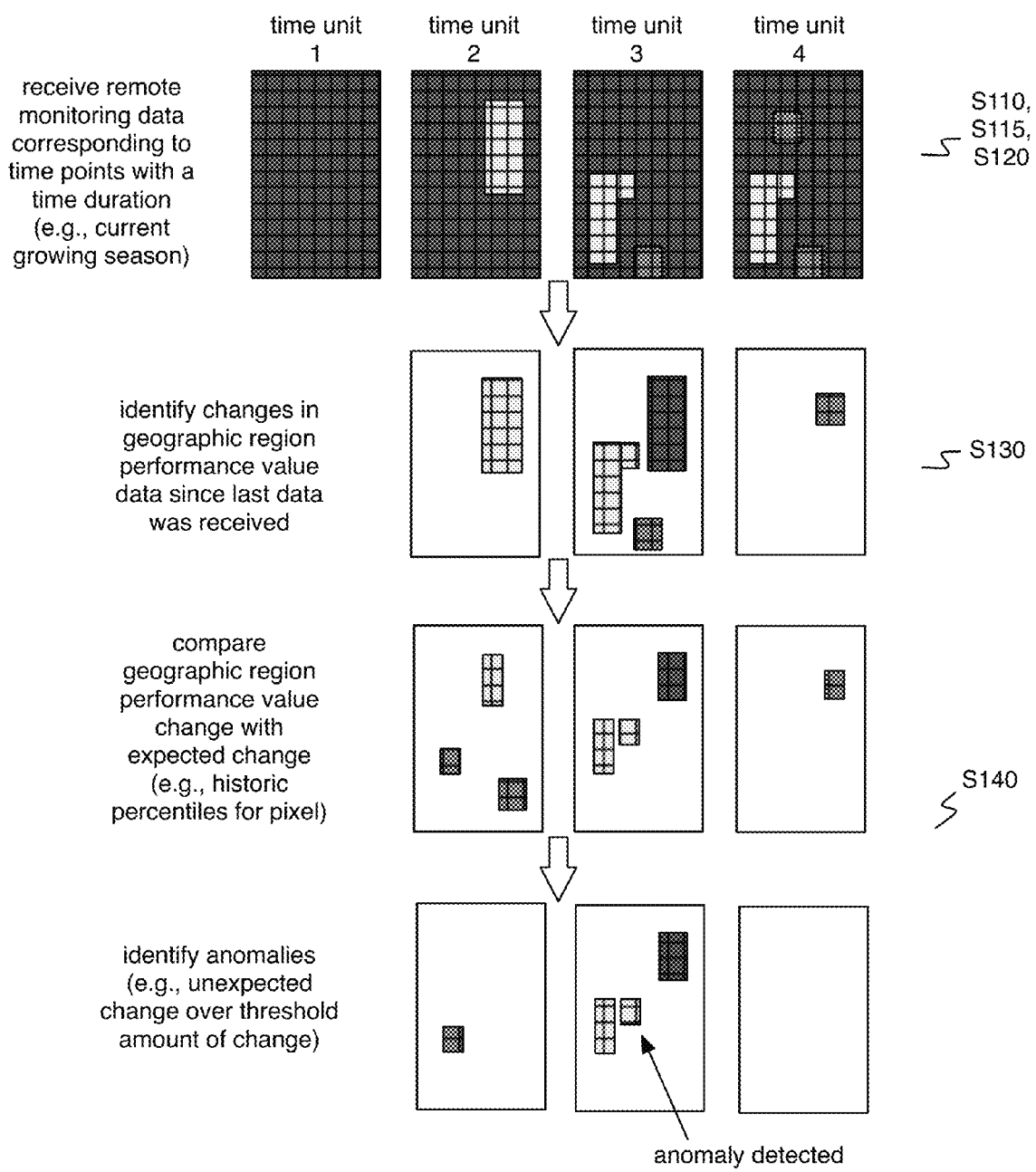
FIG. 4 is a schematic representation of the method for anomaly detection in crop health monitoring.
Figure 5:
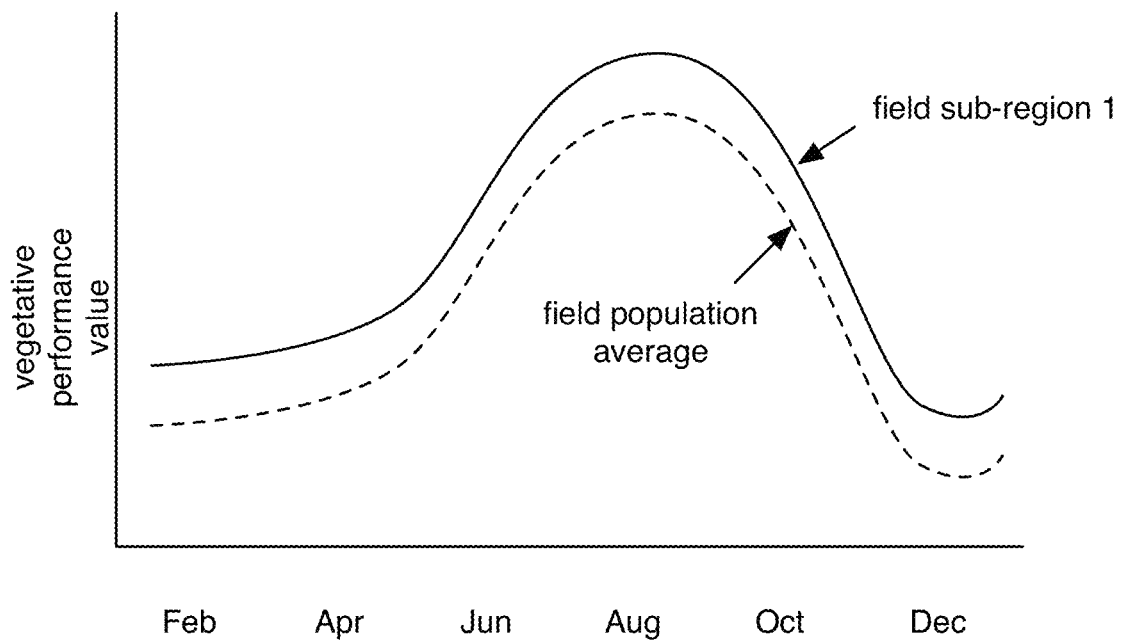
FIG. 5 is a graphical representation of comparing vegetative performance values.
Figure 6:
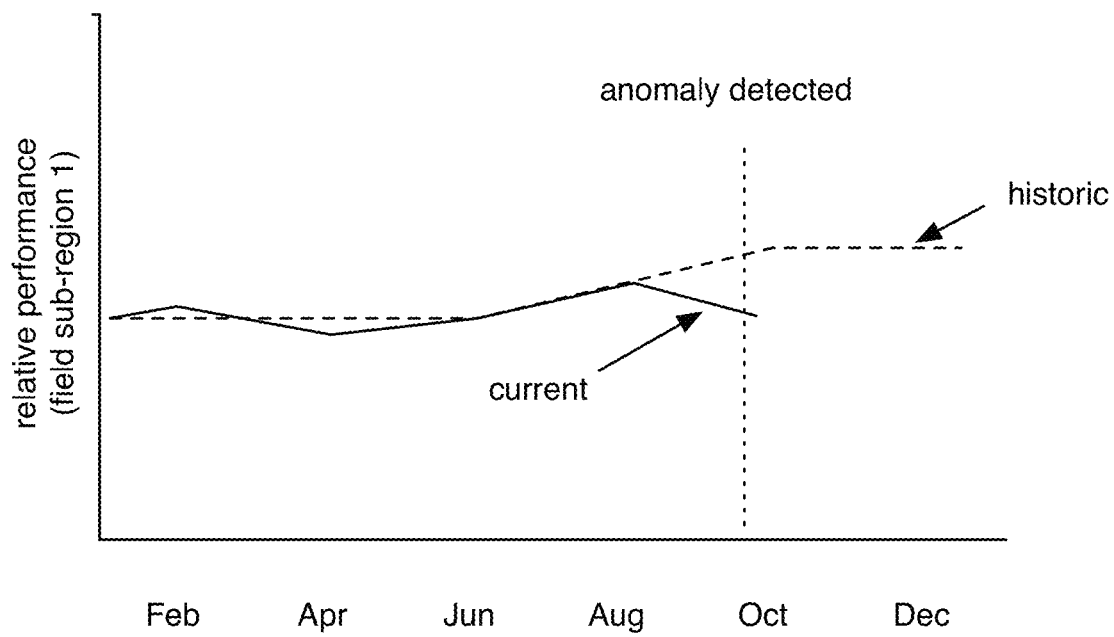
FIG. 6 is a graphical representation of comparing relative performance.

In a first specific example, representations of which are shown in FIGS. 3 and 4, the method 100 can additionally or alternatively include receiving a new image of a field from a remote field monitoring system, identifying pixels representing a physical field within the new image, each pixel representing a field sub-region, calculating a vegetative performance value for each identified pixel, determining a percentile rank for the pixel relative to the remainder of the pixels representing the field, determining a current deviation for the pixel by determining the difference between the determined pixel percentile (from the new image) and the prior pixel percentile (from a previous image), where the previous image is preferably the closest in time to the new image but can alternatively be any other suitable image, determining a historic deviation corresponding to the field sub-region by determining the difference between a first historic pixel percentile (from a first historic image) and a second historic pixel percentile (from a second historic image), and identifying an anomaly when the difference between the current deviation and the historical deviation exceeds a threshold amount.

In a second specific example, representations of which as shown in FIGS. 3 and 4, the method 100 can additionally or alternatively include receiving a new image of a field from a remote field monitoring system, identifying pixels representing a physical field within the new image, each pixel representing a field sub-region, calculating a vegetative performance value for each identified pixel, determining a percentile for each pixel, relative to the remainder of the pixels representing the field, determining a percentile change for each pixel since the previous image, where the previous image is preferably the closest in time to the new image but can alternatively be any other suitable image), comparing the percentile change for each pixel with a historical percentile change for the pixel over the comparable time unit (e.g., between the same months), and identifying an anomaly when the difference between the percentile change and the historical percentile change for a pixel exceeds a threshold amount (the anomaly threshold).

In a third specific example, the method includes: receiving a new image associated with a first recurrent time unit in a first time duration (e.g., August of 2015); calculating a vegetative performance value for each image element of the new image; for each geographic sub-region associated with an image element of the image, normalizing the vegetative performance value, calculating an actual difference between the normalized vegetative performance value and a last normalized vegetative performance value for the geographic sub-region, the last normalized vegetative performance value associated with a second recurrent time unit in the first time duration (e.g., July of 2015); calculating an expected difference between the expected normalized vegetative performance value for the first recurrent time unit and the expected normalized vegetative performance value for the second recurrent time unit; and identifying the geographic sub-region as anomalous in response to the difference between the actual change and expected change deviating beyond a threshold deviation. This variation can additionally include: identifying a set of anomalous geographic sub-regions; and classifying the set of anomalous geographic sub-regions with a first anomaly class based on features of the set, using the anomaly-detection module. This variation can additionally include: determining a crop treatment prescription to treat the identified crop health anomaly or halt crop health anomaly progression.

The method 100 is preferably iteratively performed as each new image is received throughout a time duration (e.g., a given growing season), but can alternatively be performed at any other suitable time, and include any other suitable process. However, crop health anomalies can be otherwise identified. The method 100 is preferably performed for images corresponding to different time units, but can alternatively be performed for multiple images substantially corresponding to a single time unit. However, the method 100, or any combination of steps of the method 100, can be performed for any number of images corresponding to any number and/or combination of time units. The method 100 is preferably performed in whole or in part by a remote server system that is remote from the remote monitoring system and/or monitored geographic location, but can alternatively be performed in whole or in part by a user device, or by any other suitable commuting system. The servers of the remote server system where the servers can be stateless, stateful, or have any other suitable configuration or property. The user device is preferably a mobile device associated with the user, including mobile phones, laptops, smartphones, tablets, or any other suitable mobile device. The user device is preferably connected to the remote server, where the connection is preferably a wireless connection, such as WiFi, a cellular network service, or any other suitable wireless connection, a near field connection, such as radiofrequency, Bluetooth, or any other suitable near field communication connection, or a wired connection, such as a LAN line. The user device can additionally or alternatively function as the server, such as in a distributed network system.

2. Benefits.

This method 100 can confer several benefits over conventional crop monitoring methods. First, the method 100 uses remote monitoring data (e.g., satellite images), such that entire crop fields can be monitored for anomalous events (e.g., unexpected change in geographic region performance). This is in contrast with conventional methods, in which only small portions of the crop fields can be sampled for anomalous events (e.g., disease).

Second, the method 100 can detect the crop anomalies in real- or near-real time (e.g., as the remote monitoring data is received). This is in contrast with conventional methods, which can only detect crop anomalies after the growing season is over (e.g., by using remotely sensed or otherwise determined data collected over the entirety of the growing season) or detect crop anomalies when a user affirmatively requests an anomaly analysis (e.g., when a user physically enters the crop field to check for crop failure).

Third, the method 100 can differentiate between expected changes in the crop performance (e.g., due to different crop growth stages, differences in the way the crop reacts to the soil in a given geographic sub-region, etc.) by leveraging a set of historical geographic region performance values. The set of historical geographic region performance values preferably includes historical performance metrics for each of a set of geographic sub-regions for each of a set of recurring time units (e.g., recurring calendar months. In variations leveraging the historic geographic region performance values (e.g., historic performance indices), the method 100 can assume that the crop performance of a geographical sub-region is heavily influenced by the soil performance of the geographic sub-region, and can assume that the relative soil performance of a geographic sub-region for the given recurring time unit (relative to the remainder of the geographic sub-regions for the time unit) will remain substantially constant across multiple growing years. For example, a geographic sub-region that has historically yielded crops performing in the 90th percentile in June can be expected to yield crops performing in the 90th percentile in the June of this growing season. Furthermore, in these variations, using the historic geographic region performance values to correct the measured relative geographic region performance can function to account for the expected change in the geographic region performance value between a first and second time unit (e.g., the expected change in crop performance percentile between June and July of each growing season).

Fourth, because the method 100 is remotely monitoring the entire geographic region over time, the method 100 can confer the additional benefit of recording and identifying anomaly patterns (e.g., geographic coverage pattern, spread pattern, spread rate, etc.). These patterns can subsequently be used to identify the cause of the anomaly, be used to recommend remedial treatment, and/or be used in any other suitable manner.

Fifth, the method 100 can leverage the anomaly detection capabilities to notify the user of anomalies in crop health. Notifying the user of the anomalies can include presenting a geographic region performance map to a user and informing the user of where the crop health anomaly resides on the geographic region performance map. In doing so, the method 100 can additionally or alternatively direct the user from the user's current location to the geographic source of the anomaly.

Sixth, the method 100 can enable the generation of geographic region performance maps measuring change in performance for the geographic region, where the maps possess superior image clarity and performance metrics compared to traditional yield maps and soil zone maps.

3. Method.

3.1 Receiving an Image; Mapping Image Elements.

As shown in FIGS. 1-4, the method 100 can include receiving an image including a set of image elements, the image corresponding to a time unit S110, and mapping an image element of the set of image elements to a geographic sub-region of the geographic region S115. The received image is preferably included within crop monitoring data, which can include received images, prior images, image elements (e.g., a pixel, a superpixel, a digital value, an image segment, etc.) and/or any other suitable type of data. The image is preferably associated with a geographic location (e.g., based on the location of the capturing device, the timestamp, etc.), wherein the set of image elements are preferably mapped based on the geographic location, the geographic area encompassed within the capturing device field of view, and the location of the image element within the image, or be mapped based on any other suitable data. The image elements are preferably separate (e.g., non-overlapping) portions of the image, wherein the image can be split into a matrix of image elements, but can alternatively be overlapping or otherwise interrelated portions of the image. Examples of image elements include pixels, objects, or any other suitable image element.

The image can be received and/or mapped using the system and method disclosed in U.S. application Ser. No. 15/012,762 filed 1 Feb. 2016 and titled "SYSTEM AND METHOD FOR FIELD VARIANCE DETERMINATION," which is herein incorporated in its entirety by this reference. However, the image can be received and/or the image elements mapped to geographic sub-regions and/or locations in any other suitable manner.

3.2 Determining a Geographic Region Performance Value.

Determining a geographic region performance value S120 functions to generate a metric (e.g., expected performance value, reference performance value, etc.) to measure land performance of a geographic sub-region and/or geographic region for comparison with land performance at other times. Determining a geographic region performance value S120 can additionally or alternatively include determining a vegetative performance value for an image element S124, mapping an image element to a crop type S126, and/or comparing vegetative performance values S128.

In one variation, determining a vegetative performance value for an image element includes: splitting the image into a set of image elements, for each image element, determining a respective visual signal parameter from the image element (e.g., intensity of a given light wavelength); and calculating a vegetative performance value from the visual signal parameter (e.g., calculating a WDRVI value for the pixel). Determining the vegetative performance value can additionally include storing the determined vegetative performance value in association with the geographic sub-region associated with the respective image element. Determining the vegetative performance value can additionally include: identifying image elements and/or geographic sub-regions growing the same crop type or varietal and normalizing the vegetative performance values for each of the identified image elements and/or geographic sub-regions based on the remainder of the identified image elements and/or geographic sub-regions. Determining the vegetative performance value can additionally include: generating a yield proxy map by mapping the normalized vegetative performance values based on the respective geographic sub-region or respective geographic locations.

In a second variation, the vegetative performance value is determined using the method and system disclosed in U.S. application Ser. No. 15/012,762 filed 1 Feb. 2016 and titled "SYSTEM AND METHOD FOR FIELD VARIANCE DETERMINATION," which is herein incorporated in its entirety by this reference. However, the vegetative performance values can be otherwise determined.

3.3 Identifying a Crop Health Anomaly.

As shown in FIGS. 1-4, identifying a crop health anomaly S140 functions to identify unexpected performance characteristics of at least one geographic sub-region and/or region. Identifying a crop health anomaly can additionally or alternatively include defining the geographic sub-region as an anomalous geographic sub-region S145, and/or identifying the crop health anomaly based on supplemental data S148.

Crop health anomalies can be caused by pests, environmental effects (e.g., unexpected weather), crop inputs (e.g. changes in fertilizer application, changes in seeding), and/or any other suitable cause. Any number of crop health anomalies can be determined for any number and/or combination of geographic sub-regions, geographic regions, and/or any suitable geographic area. The crop health anomaly is preferably identified S140 in response to geographic region performance value change determination S130, but can additionally and/or alternatively be performed at any suitable time and/or in relation to any suitable step of the method 100.

A crop health anomaly is preferably identified based on comparison of geographic region performance values. Crop health anomalies are more preferably identified when actual geographic region performance characteristics deviate from expected characteristics beyond a threshold deviation, but crop health anomalies can additionally or alternatively be identified based on any other suitable unexpected characteristics (e.g., soil characteristics, crop characteristics, weather characteristics, etc.) associated with the geographic sub-region, geographic region, and/or geographic area.

Geographic region performance values used in identifying crop health anomalies can be individual geographic region performance values, composite (e.g., combined) geographic region performance values, predetermined values, automatically determined values, user-determined values, and/or an other suitable type of geographic region performance value. Combined geographic region performance values are preferably associated with a common time instance (e.g., a common month or day) within a time duration (e.g., a growing season or calendar year). For example, all or a subset of available geographic region performance values corresponding to time instances occurring within a recurrent time unit of a time duration can be aggregated together. In a specific example, all geographic region performance values corresponding to dates (time instances) falling within November (the recurrent time unit) of the current growing season (the time duration) can be combined (e.g., averaged) to form the geographic region performance values for November. In another specific example, a combined geographic region performance value can be a combination of the values associated with different days within the same month of July of a current growing season. However, identifying a crop health anomaly can additionally or alternatively be based on any other suitable data.

3.3. A Identifying a Crop Health Anomaly Based on a Geographic Region Performance Value.

In a first variation, identifying a crop health anomaly S140 can include identifying the anomaly based on an actual geographic region performance value and an expected geographic region performance value for the same recurrent time frame. The actual geographical performance value preferably corresponds to a current instance of a recurrent time unit within a current time duration (e.g., August of the current growing season). The expected geographic region performance value preferably corresponds to a historic instance of the recurrent time unit within a historic time duration (e.g., August of a historic growing season). However, the actual and the expected performance values can correspond to any suitable time instances, time units, and/or time durations.

In one example of the first variation, identifying the anomaly S140 can be based on the actual geographic region performance value for the geographic sub-region differing beyond a threshold amount from the expected geographic region performance value. In a specific example, a crop health anomaly can be identified based on the deviation between a first geographic region performance value corresponding to April 22 of the current growing season, and a second geographic region performance value corresponding to April 22 of a previous growing season. In another specific example, identifying the crop health anomaly S140 can include determining the difference between the current percentile ranking (e.g., with respect to geographic region performance values of the received image) for the geographic sub-region (or representative pixel) and the historic percentile ranking for the geographic sub-region. However, the anomaly can be otherwise identified based on the actual geographic region performance value and an expected geographic region performance value for the recurrent time frame.

3.3.B Identifying a Crop Health Anomaly Based on a Geographic Region Performance Value Change.

In a second variation, identifying the crop health anomaly S140 is based on an actual geographic region performance value change over time and an expected geographic region performance value change over time. An anomaly (e.g., an unexpected change) is preferably identified when the geographic region performance value change deviates from the expected geographic region performance value change beyond a threshold amount. The threshold amount can be generic (e.g., the same for all fields), specific to the field, specific to the sub-region, specific to the crop currently being grown on the field, specific to the management practices, or otherwise determined. However, the crop health anomaly can be determined in any other suitable manner. Identifying changes in the performance of the field that do not stem from expected changes enables identification of unexpected changes due to the crop type (e.g., over the growing season), unexpected seasonal changes in the performance of the soil or geographic region, and/or any other type of unexpected change due to any suitable cause. This can assume that the average relative geographic sub-region performance variance pattern remains substantially the same year over year.

An actual and an expected geographic region performance value change is preferably determined for each geographic sub-region represented by an image element (e.g., pixel) in the image, but geographic region performance value changes can alternatively be determined for a subset of the geographic sub-regions represented within the image, for the geographic region as a whole, or for any other suitable geographic area. The actual and the expected geographic region performance value changes are preferably associated with the same geographic sub-region, but can additionally or alternatively be associated with different geographic sub-regions, different geographic region, and/or any suitable geographic area.

An actual geographic region performance value change is preferably calculated based on a first geographic region performance value determined as in S120 and a secondary geographic region performance value associated with a secondary image (e.g., a second image received in the past, a second image to be received in the future, a composite image, etc.). Alternatively, the first geographic region performance value can be compared against a secondary geographic region performance value associated with the same image (e.g., a geographic region performance value associated with a different geographic sub-region present in the image, a geographic region performance value associated with an image element corresponding to a different time unit, etc.), or against a geographic region performance value not associated with an image (e.g., a predetermined reference geographic region performance value, an automatically determined geographic region performance value, a user-influenced geographic region performance value, etc.), but the geographic region performance value change can be determined based on any suitable combination and/or number of geographic region performance values. An actual geographic region performance value change is preferably determined by calculating the difference between the first geographic region performance value and the other geographic region performance value, but the geographic region performance value change can be otherwise determined.

A geographic region performance value change is preferably determined between two geographic region performance values mapped to a common geographic sub-region. Alternatively, a geographic region performance value change can be determined based on geographic region performance values mapped to different geographic sub-regions, but geographic region performance value changes can be calculated with respect to any number and/or combination of geographic region performance values mapped to any number and/or combination of geographic sub-regions, geographic regions, and/or any suitable geographic area.

Identifying the crop health anomaly S140 can include calculating an actual geographic region performance value change. The actual geographic region performance value change is preferably between a first and a second geographic region performance value associated with a first and a second image, respectively, wherein the first image can correspond to a first instance of a first recurring time unit (e.g., the calendar moth of August), and the second image cam correspond to a first instance of a second recurring time unit (e.g., the calendar month of July). The first recurring time unit is preferably different from the second recurring time unit (e.g., July and August, respectively), but can alternatively be the same time unit as the second recurring time unit (e.g., July and July, respectively). The first instance of the second recurring time unit (e.g., July 2015) is preferably earlier than the first instance of the first recurring time unit (e.g., August 2015). Alternatively, the first instance of the second recurring time unit can be substantially similar in time (e.g., concurrent with) or after the first instance of the first recurring time unit. However, any suitable combinations and/or types of time instances and/or time units can be associated with the first and/or the second geographic region performance values.

The first instances of the first and the second recurring time units are preferably sequential (e.g., January and February of the current growing season, June 1 and June 2 of a current calendar year, etc.), but can alternatively be non-sequential. However, instances of the recurring time unit can relate to one another in any suitable fashion. The first instances of the first and the second recurring time units are preferably within a common or contiguous time duration (e.g., growing season, calendar year, etc.). For example, for a current growing season, the first instance of the first recurrent time unit (e.g., the calendar month of February) can correspond to February within the current growing season, and the first instance of the second recurrent time unit (e.g., the calendar month of March) can correspond to March within the current growing season. Alternatively, the time instances corresponding to the first and the second geographic region performance values can be within different time durations. For example, a first and a second time duration can be defined as a first and a second calendar year, where the first geographic region performance value corresponds to April 1 of the first calendar year, and the second geographic region performance value corresponds to April 1 of the second calendar year. However, the geographic region performance values used in determining the geographic region performance value change can otherwise relate in any suitable fashion to any number, combination, and/or type of time durations.

The expected geographic region performance value change is preferably determined from previously determined historic geographic region performance values corresponding to the first and second recurring time units. The expected geographic region performance value change is preferably determined as the difference between a first and second historic geographic region performance value corresponding to the geographic region (or sub-region) for the first and second recurring time units, respectively, but can otherwise be determined. The historical set of geographic region performance values preferably includes geographic region performance values for each geographic sub-region for each of a set of recurring time units. The historical set of geographic region performance values are preferably an aggregate of geographic region performance values across multiple time durations (e.g., across multiple growing seasons), such that the historical set is not specific to any one time duration. However, the historical set can be specific to a specific time duration. In a specific example, the historical set of relative performance values includes a first and a second historical geographic region performance value. The first and the second historical geographic region performance values are mapped to a common geographic sub-region. The first and the second historical geographic region performance values correspond to a January and a February, respectively, of a historic growing season. However, the historical set of geographic region performance values can additionally or alternatively include any other suitable information.

In a first embodiment of the second variation, identifying the crop health anomaly S140 includes: calculating an actual performance change between a first and a second geographic region performance value corresponding to instances of a first and a second recurrent time unit within a current time duration; calculating an expected change between a first and a second historic geographic region performance value corresponding to instances of the first and the second recurrent time unit within at least one historic time duration; and comparing the actual and expected performance changes. In a first example, the actual geographic region performance value change is determined as the difference between a first and a second geographic region performance value corresponding to a June and a July of the current growing season. In this specific example, the expected geographic region performance value change is determined as the difference between a first and a second historic geographic region performance value corresponding to June and July of at least one previous growing season.

In a second embodiment of the second variation, identifying the crop health anomaly S140 includes: calculating an actual performance change between a current performance value and a first historic performance value corresponding to instances of a first recurrent time unit within different growing seasons (e.g., the same recurrent time frame in different growing seasons); calculating an expected change between a prior performance value and a second historic performance value corresponding to instances of a second recurrent time unit within different growing seasons; and comparing the actual and expected performance changes. The first and second recurrent time units are preferably different, but can alternatively be the same. As an illustration of the second example, an expected geographic region performance value change can be calculated as the difference between the geographic region performance value associated with September of the current growing season, and a historic geographic region performance value associated with September of at least one historic growing season. Identifying the crop health anomaly could then be based on calculating the difference between the expected geographic region performance value change and the actual geographic region performance value change determined, in the illustration, as the change between a current geographic region performance value associated with October of the current growing season, and a second historic geographic region performance value associated with October of at least one historic growing season. The second embodiment can function to accommodate for anomalies that occurred within the geographic sub-region earlier in the growing season, and the anomalies' subsequent effects throughout the remainder of the growing season.

3.3.0 Defining an Anomalous Geographic Sub-Region.

In a third variation, identifying a crop health anomaly S140 can include: identifying a set of anomalous geographic sub-regions and determining that the set of anomalous geographic sub-regions is indicative of a crop health anomaly based on a characteristic of the set of anomalous geographic sub-regions S145.

Identifying an anomalous geographic sub-region functions to define at least one anomalous geographic sub-region from which a crop health anomaly can be identified. The anomalous geographic sub-region can be included in the set of anomalous geographic sub-regions. Alternatively, the anomalous geographic sub-region can stand alone, but can otherwise be related to geographic areas captured by the image. The anomalous geographic sub-region is preferably the same size as the geographic area represented by an image element, but can alternatively be larger than that represented by an image element (e.g., larger than a pixel), smaller, or be any other suitable size.

In a first variation, actual and expected performance values and/or performance value changes can be calculated and compared for each geographic sub-region using the method discussed above (for identifying anomalous image elements and/or corresponding geographic sub-regions), wherein the geographic sub-region is used as the unit of comparison instead of an image element. In a second variation, anomalous geographic sub-regions can be identified from the underlying image elements, wherein the underlying image element is identified as anomalous. However, the anomalous geographic sub-region can be identified in any other suitable manner. However, any suitable geographic area and/or its corresponding image element (e.g., a pixel corresponding to a geographic sub-region with unexpected performance) can be can be defined as anomalous in any suitable fashion.

Determining that the set of anomalous geographic sub-regions is indicative of a crop health anomaly based on a characteristic of the set of anomalous geographic sub-regions S145 can function to reduce the probability of false positives (e.g., notifying users of a crop health anomaly when none exists). The set of anomalous geographic sub-regions from which the crop health anomaly is identified preferably includes geographic sub-regions and/or image elements that are captured within a received image. Alternatively, the set of anomalous geographic sub-regions can include geographic sub-regions excluded or partially included in the content of the image received as in S110, but the set of anomalous geographic sub-regions can include any suitable geographic sub-region possessing performance characteristics deviating from expected.

In a first variation, the set of anomalous geographic sub-regions can be identified as a crop health anomaly based on the relative locations of anomalous geographic sub-regions with respect to other anomalous geographic sub-regions within the set, such as whether anomalous geographic sub-regions are positioned contiguously, within a predetermined geographic or image distance of another anomalous geographic sub-region (e.g., when the anomalous geographic sub-regions within the set exhibit a predetermined concentration), and/or substantially near one another. For example, a crop health anomaly can not be identified if a given pixel is mapped to an anomalous geographic sub-region bordered by normal geographic sub-regions, but a crop health anomaly can be identified if the anomalous geographic sub-region is bordered exclusively by other anomalous geographic sub-regions (e.g., a cluster of pixels are identified as anomalous). In a second variation, the anomaly can be identified based on the number and/or density of contiguous and/or non-contiguous anomalous geographic sub-regions. In a third variation, the anomaly can be identified when the geographic pattern or distribution of anomalous geographic sub-regions within the geographic region (or virtual representation thereof) substantially matches a known pattern indicative of a crop health anomaly or is otherwise classified as a crop health anomaly. However, crop health anomalies can be identified S145 based on any suitable relationship between any number and/or combination of anomalous geographic sub-regions, normal geographic sub-regions, and/or other suitable geographic areas or data.

3.3.D Identifying an Anomaly Based on Supplemental Data.

In a fourth variation, as shown in FIG. 2, identifying a crop health anomaly S140 can additionally or alternatively include identifying the crop health anomaly based on supplemental data S148, which functions to consider supplemental data in determining whether an anomaly in crop health exists. Supplemental data types can include soil data (e.g., soil texture, soil hydraulic properties, soil organic matter, etc.), weather data (e.g., daily temperature, precipitation, radiation, etc.), crop management data (e.g., user-inputted data, historic seeding prescriptions, treatment application system measurements, etc.), and/or any other suitable data type supplemental to geographic region performance value data. Supplemental datasets can be received from a user, a third party (e.g., a service supplying remote images of the geographic region) and/or determined (e.g., predetermined or automatically determined based on time, geographic area location, etc.) by any suitable entity in any suitable fashion. For example, a user, at a user interface of a user device, can submit historic seeding data for a geographic sub-region, and the supplemental data can be used in identifying the crop health anomaly. A received supplemental dataset can be associated with the actual geographic region performance value change, where the supplemental dataset comprises at least one of a soil characteristic, a weather characteristic, and a user input. The supplemental dataset can be compared to a historic supplemental dataset associated with the expected geographic region performance value change, and identifying the crop health anomaly S140 can be identified by comparing the supplemental dataset to the historical supplemental dataset. Alternatively, the supplemental dataset can be associated with both the actual and the expected geographic region performance value change. However, the supplemental dataset and/or the historic supplemental dataset can include any suitable supplemental characteristic, and/or can be associated with any suitable type of data.

3.3.E Generating an Anomaly-Determination Model.

In a fifth variation, identifying the crop health anomaly can include generating an anomaly-determination model for identifying the crop health anomaly. The anomaly-determination model (anomaly-determination module) is preferably generated based on feature types, including: any type of geographic region performance data (e.g., vegetative performance values, geographic region performance values, changes in geographic region performance values, etc.), identified anomalous geographic sub-regions (e.g., number of anomalous areas, pattern of anomalous areas, frequency and/or degree of contiguous anomalous areas, etc.) and/or supplemental data (e.g., soil data, weather data, crop management data, etc.). However, an anomaly-determination model for identifying crop health anomalies can otherwise be generated. Subsequent to analyzing a received image for crop health anomalies (e.g., after comparing the actual and expected geographic region performance value changes), the generated model can be updated with data associated with the received image. For example, the method 100 can additionally or alternatively include updating the expected geographic region performance value change for the geographic sub-region based on the actual geographic region performance value change.

The anomaly-determination model preferably leverages a machine learning algorithm that is trained with a training dataset including training samples, each training sample associated with a set of features, each feature corresponding to a feature type. Alternatively, any type of model can be employed in identifying crop health anomalies. In examples, the machine learning algorithm can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

In an example where the model is generated based on a machine learning algorithm, the labels for the training data are preferably binary, indicating whether individual training samples are associated or not associated with a crop health anomaly. Alternatively, the labels can be non-binary (e.g., labels indicating probability of crop health anomaly, different labels for different types of crop health anomalies, labels indicating an unexpected change in performance, etc.).

In a first illustration of the example, an image is received as in S110, geographic region performance values and geographic region performance value changes are determined for image elements of the image, supplemental data is received and associated with the image elements, and the data (e.g., the performance data and the supplemental data) is used as a test sample upon which the model (e.g., generated from historic performance data and historic supplemental data) is run, where the model outputs whether the test data is associated with a crop health anomaly. The test data can subsequently be used in updating the machine learning model by retraining the model on training data that now includes the test data. In a second illustration of the example, a set of anomalous geographic sub-regions can be identified in response to performance values for those sub-regions differing from expected performance values beyond a threshold amount. Characteristics (e.g., geographic pattern, change in performance values of the sub-regions over time, number of anomalous sub-regions, etc.) of the set of anomalous geographic sub-regions can be used as features to use with a machine learning model.

However, machine learning models for identifying crop health anomalies can be generated and/or applied in any suitable manner.

3.4 Diagnosing the Crop Health Anomaly.

As shown in FIG. 2, the method 100 can additionally or alternatively include diagnosing the crop health anomaly S150, which functions to assess the cause or causes of the crop health anomaly. Diagnosing the crop health anomaly S150 can include recording and identifying anomaly patterns (e.g., geographic coverage pattern, spread pattern, spread rate, etc.), that can subsequently be used to identify the cause of the anomaly, be used to recommend remedial treatment, and/or be used in any other suitable manner. The crop health anomaly can additionally or alternatively be diagnosed based on supplemental data (e.g., soil data, weather data, crop treatment data, user input, etc.). The diagnosed cause of the crop health anomaly is preferably associated with a confidence level indicating a probability that the diagnosed cause is the actual cause of the crop health anomaly. Alternatively, multiple potential causes can be identified and ranked in relation to the probability that the respective potential cause is the actual cause of the crop health anomaly. However, any number of potential causes and/or confidence levels associated with the potential causes can be identified for any number of crop health anomalies. The crop health anomaly is preferably diagnosed S150 at a remote server, but can additionally or alternatively be diagnosed at a user device and/or any other suitable component. The crop health anomaly is preferably diagnosed by the anomaly-determination model, but can alternatively be otherwise diagnosed.

Each crop health anomaly stored by the system can be associated with a crop health anomaly profile, which can be used to diagnose the instantaneous crop health anomaly. The crop health anomaly profile is preferably predetermined (e.g., for known crop health anomalies) and retrieved from computer storage, but can alternatively be dynamically determined (e.g., for the instantaneous crop health anomaly). The crop health anomaly profile can associate a set of characteristics with a crop health anomaly type. The crop health anomaly profile can indicate a type of anomaly (e.g., unexpectedly poor soy yield for this geographic subregion at this time of the growing season, an unexpected rate of decrease in yield over time, etc.), a cause of anomaly (e.g., insufficient amount of corn seeding, pest infestation, etc.), a pattern of anomalies (e.g., anomalies in geographic sub-regions geometrically forming parallel, adjacent lines), and/or any other suitable characteristics of crop health anomalies. In an example, the crop health anomaly profile can indicate an anomaly type of a lower than expected corn yield in January of the current growing season. The cause of the anomaly can be identified as insufficient nitrogen application.

In a first variation, diagnosing the crop health anomaly can include: determining feature values for a set of features from the set of anomalous geographic sub-regions (and/or image elements); identifying a set of candidate anomalies; for each candidate anomaly, calculating the probability that the set of anomalous geographic sub-regions exhibits the respective candidate anomaly based on the feature values; and selecting the candidate anomaly with the highest probability as the diagnosed anomaly.

In a second variation, diagnosing the crop health anomaly can include: creating a virtual representation of the geographic region (e.g., virtual map, matrix, array, data structure, etc.), wherein anomalous geographic sub-regions are differentiated from normal geographic sub-regions (e.g., visually, numerically, etc.); extracting a distribution pattern of anomalous geographic sub-regions from the virtual representation; matching the distribution pattern to a set of predetermined patterns, each of the set of predetermined patterns associated with a candidate anomaly; and selecting candidate anomaly associated with the pattern best matching the distribution pattern as the diagnosed anomaly. However, the crop health anomaly can be otherwise diagnosed.

3.5 Determining a Crop Treatment.

The method 100 can additionally or alternatively include determining a crop treatment S160, which functions to determine a treatment tailored to addressing an identified crop health anomaly. Determining a crop treatment S160 is preferably based on the crop health anomaly diagnosis, but can additionally or alternatively be based on crop health anomalies otherwise identified, a target yield for the geographic region, and/or any other suitable data. The crop treatments are preferably determined for the geographic sub-region associated with the identified crop health anomaly, but can additionally or alternatively be determined for any suitable geographic sub-region, geographic region, and/or geographic area.

Determined crop treatments are preferably presented to a user at a user device as in S170. Alternatively or additionally, a user can be notified through other suitable means, but notification can otherwise be omitted. The crop treatment can include a crop input prescription (e.g., a seeding prescription, a fertilizer prescription, a fungicide prescription, etc.), crop treatment instructions, and/or any other suitable information for implementing the crop treatment recommendation. Any number of crop treatments can be determined for any number and/or combination of geographic sub-regions, geographic regions, and/or geographic areas. The crop treatment can be determined at a remote server, but can additionally or alternatively be identified at a user device and/or any other suitable component. The crop treatment can be determined S160 in response to diagnosing the crop health anomaly, but can otherwise be determined before, after, in response to, or in any other suitable relation to any suitable step of the method 100.

In a first variation, the crop treatment is selected based on the diagnosed crop anomaly. In a first embodiment, the recommended treatment is the treatment recommended in the respective profile for the diagnosed crop health anomaly or class thereof. In a second variation, crop treatments can be determined based on performance values, performance value changes, deviations from expected performance values, and/or deviations from expected performance value changes, irrespective of whether geographic sub-regions corresponding to the performance values are associated with a crop health anomaly. In a third variation, crop treatments can be recommended based on the crop plan for the geographic region (field) and the crop anomaly diagnosis. For example, the recommendation can include adjusting the parameters of the next-planned crop treatment to treat the anomaly. In a fourth variation, crop treatments can be recommended based on the treatments that a subset of users (e.g., users with high yield, users that have successfully treated the anomaly or halted anomaly progression) have historically applied to treat similar anomalies. In a fifth variation, the recommended crop treatments can be those recommended by a manufacturer (e.g., seed provider). However, crop treatments can otherwise be determined.

3.6 Notifying a User.

The method 100 can additionally or alternatively include notifying the user S170, which functions to inform a user of crop health anomalies, treatments, and/or circumstances surrounding crop health anomalies. Notifying the user S170 can include presenting identified crop health anomalies to the user at a user device, but can alternatively be otherwise provided. The anomaly notification is preferably presented on the user device in response to identification of a crop health anomaly as in S140, but can alternatively or additionally be presented in response to or in relation to any other suitable step of the method 100. A notification is preferably presented to the user for every identified crop health anomaly (e.g., a first notification for a first crop health anomaly identified with respect to the current image, a second notification for a second crop health anomaly identified with respect to a future image). Alternatively, notification frequency can be user-selected. However, any number and/or type of notification can be presented to the user for any number and/or type of identified crop health anomaly.

In a first variation, the identified crop health anomaly is graphically presented on the user device S174. The crop health anomaly can be displayed along with notifications of the crop health anomaly. Alternatively, an option to display the crop health anomaly can be presented in a notification, and the crop health anomaly can be displayed in response to an affirmative user response to the option.

In one example of the first variation, a color-coded map of the geographic region can be generated and displayed, the map comprising a plurality of map elements, where each map element corresponds to a geographic sub-region, and where each map element is associated with a color indicative of a difference between the actual geographic region performance value change and an expected geographic region performance value change for the respective geographic sub-region. Anomalous geographic sub-regions can be graphically represented in a different color from non-anomalous geographic sub-regions.

In the first variation, the method 100 can additionally include: identifying the geographic sub-region (e.g., pixel) exhibiting the anomaly, identifying secondary geographic sub-regions adjacent the anomalous geographic sub-region, determining secondary anomalous geographic sub-regions based on the respective relative performance changes, and displaying the secondary anomalous geographic sub-regions. The secondary geographic sub-regions can be contiguous the anomalous geographic sub-region, within a threshold distance or number of pixels from the anomalous geographic sub-region, or otherwise associated with the anomalous geographic sub-region. The secondary anomalous geographic sub-regions can be the secondary geographic sub-regions for which the respective geographic region performance value changes exceed threshold changes. In a specific example, an anomalous geographic sub-region is identified when the actual geographic region performance value change deviates more than 50% from the expected geographic region performance value change, and a secondary anomalous geographic sub-region is identified for an adjacent, secondary geographic sub-region when the respective geographic region performance value change deviates from the respective expected geographic region performance value change by less than 50% but more than 25% (a secondary threshold value). The identified secondary anomalous geographic sub-region can be represented by the anomalous color, or by a secondary color. However, anomalous geographic sub-regions can be otherwise presented to the user.

As shown in FIG. 7A, in the first variation, graphically presenting the crop health anomaly on the user device can additionally or alternatively include directing the user to the crop health anomaly S175. The user can be directed from their location (e.g., using GPS coordinates the user device has shared) to the geographic sub-region associated with the identified crop health anomaly. Alternatively, the user can input a desired starting point, and a route can be generated from the starting point to the geographic sub-region. However, any suitable route can be generated from any suitable starting point to any suitable geographic area associated with the crop health anomaly. The directions to the crop health anomaly are preferably graphically presented on the color-coded map of the geographic region. Alternatively, the directions to the crop health anomaly can be presented textually (e.g., in the form of text notifications), orally (e.g., in the form of audio), and/or in any other suitable form.

As shown in FIG. 7B, in a second variation, notifying the user can include presenting the diagnosis of the crop health anomaly S176. Notifying the user can be performed after diagnosing the crop health anomaly S150, but can otherwise be performed. The diagnosis of the crop health anomaly can be presented in conjunction with the crop health anomaly (e.g., in conjunction with a performance heat map of the geographic region with the anomaly highlighted), the crop treatment (e.g., a diagnosis of the cause of the anomaly and a treatment to rectify that cause), and/or any other suitable information. However, the diagnosis of the crop health anomaly can be presented before, after, or in conjunction with any suitable type of data.

Presenting the diagnosis of the crop health anomaly S176 can additionally include presenting an option for the user to verify the identified crop health anomaly. The option can allow the user to confirm or deny the presence of the anomaly, the anomaly diagnosis, the usability of the recommended treatment, and/or any other suitable data that can be verified. The option can be presented along the crop health anomaly, upon the user arriving at the location of the crop health anomaly, and/or any other suitable time. A user's response to the option can be used with training data in generating or updating a model (e.g., a machine learning model) for identifying a crop health anomaly. For example, upon receipt of a positive response from the user (e.g., anomaly type verification), the anomaly-determination model can be reinforced. Upon receipt of a negative response and/or receipt of a second anomaly identifier from the user, the anomaly-determination model can be recalibrated using the second anomaly identifier and previously calculated parameter value set and/or other data. However, the user response to the diagnosed anomaly notification can be otherwise processed. However, user responses to the option can be otherwise used.

Receiving the user response can additionally include verifying that the user performed an in-field verification prior to accepting the user verification. Verifying that the user performed an in-field verification can be based on a user device location (e.g., received from the user device's location sensor, such as a GPS), or be based on any other suitable data. In a first example, upon identifying a crop health anomaly, the anomaly and a route to the anomaly can be presented to the user. When the user reaches a geographic sub-region associated with the anomaly, an option to verify the presence or lack of the crop health anomaly can be presented to the user. The user can investigate the crops, verify the presence of the crop health anomaly, and affirmative respond to the option. The user's feedback can then be used in updating a machine learning model for identifying future crop health alerts (e.g., a machine learning model used specifically for the user, for multiple users, for a field, etc.)

In a second example, the system can refuse the anomaly diagnosis verification unless the location history of the user (or user device) indicates that the user visited the anomalous geographic area between diagnosis presentation to the user and acceptance or rejection of the diagnosis verification. However, in-field user verification of the anomaly can be otherwise validated.

As shown in FIG. 7C, in a third variation, notifying the user can include presenting a crop treatment S177. Notifying the user can be performed after determining the crop treatment S160, but can otherwise be performed. In an example of the third variation, presenting the crop treatment can include presenting an option for the user to confirm or deny the recommended crop treatment. A user response to the crop treatment recommendation can be received, and the crop treatment can be automatically initiated (e.g. through communicating treatment instructions to crop input applicators) in response to a user confirmation of the recommended crop treatment.

An alternative embodiment preferably implements the above methods in a computer-readable medium storing computer-readable instructions. The instructions are preferably executed by computer-executable components preferably integrated with a field anomaly detection system. The field anomaly detection system can include remote monitoring system configured to record remote data (e.g., an image) of a field, an indexing system configured to calculate an index indicative of crop performance for each geographic sub-region of the field, a comparison system configured to compare the vegetative index for new field data with historic field data, and an anomaly detection system configured to identify any geographic sub-region(s) exhibiting unexpected crop performance. The computer-readable medium may be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device.

Although omitted for conciseness, the preferred embodiments include every combination and permutation of the various system components and the various method processes.

As a person skilled in the art will recognize from the previous detailed description and from the figures and claims, modifications and changes can be made to the preferred embodiments of the invention without departing from the scope of this invention defined in the following claims.

We claim:

1. A method for monitoring crop health of a geographic region, the method comprising:
   receiving a first image comprising a set of image elements, the first image corresponding to a first instance of a first recurrent time unit;
   mapping a first image element of the set of image elements to a geographic sub-region of the geographic region;
   generating a vegetative performance value for the first image element;
   mapping the first image element to a crop type;
   normalizing the vegetative performance value with respect to remaining vegetative performance values associated with a subset of the set of image elements, wherein the subset of image elements is mapped to the crop type;
   generating a first geographic region performance value for the first image element based on the normalization of the vegetative performance value;
   calculating an actual geographic region performance value change between the first geographic region performance value and a second geographic region performance value, the second geographic region performance value associated with a second image element of a second image, the second image corresponding to a first instance of a second recurrent time unit, wherein the second image element is mapped to the geographic sub-region;
   determining an expected geographic region performance value change based on a third and a fourth geographic region performance value, wherein the third geographic performance value is associated with a third image corresponding to a second instance of the first recurrent time unit, and wherein the fourth geographic region is associated with a fourth image corresponding to a second instance of the second recurrent time unit;
   defining the geographic sub-region as an anomalous geographic sub-region of a set of anomalous geographic sub-regions, in response to the actual geographic region performance value change differing beyond a predetermined threshold from the expected geographic region performance value change for the geographic sub-region; and identifying a crop health anomaly based on the set of anomalous geographic sub-regions.

2. The method of claim 1, wherein the first and the second recurrent time units are a first and a second month of a growing season, respectively.

3. The method of claim 1, wherein the first instances of the first and the second recurrent time units are within a first growing season, and wherein the second instances of the first and second recurrent time units are within a reference growing season representative of historic growing seasons.

4. The method of claim 3, wherein the first recurrent time unit corresponds to a first common calendar month, and wherein the second recurrent time unit corresponds to a second common calendar month.

5. The method of claim 1, further comprising notifying a user of the crop health anomaly in response to identification of the crop health anomaly.

6. The method of claim 5, wherein notifying the user comprises:

generating a color-coded map of the geographic region comprising a plurality of map elements, wherein each map element of the plurality corresponds to a geographic sub-region of the geographic region, wherein each map element is associated with a color indicative of a difference between the actual geographic region performance value change and an expected geographic region performance value change for the respective geographic sub-region;

displaying the color-coded map on a user device associated with the user.

7. The method of claim 5, wherein notifying the user comprises directing the user to the geographic sub-region.

8. The method of claim 1, further comprising updating the expected geographic region performance value change for the geographic sub-region based on the actual geographic region performance value change.

9. A method for monitoring crop health of a geographic region, the method comprising:

receiving a first image comprising a set of image elements, the first image corresponding to a first time unit;

mapping a first image element of the set of image elements to a geographic sub-region of the geographic region;

determining a first geographic region performance value for the geographic sub-region based on the first image element;

generating a combined geographic region performance value, comprising combining the first geographic region performance value with a second geographic region performance value associated with a second image element of a second image corresponding to a second time unit, wherein the second geographic region performance value is determined by combining a third and a fourth geographic region performance value, wherein the third geographic region performance value is associated with a third image element of a third image corresponding to a third time unit, and wherein the fourth geographic region performance value is associated with a fourth image element of a fourth image corresponding to a fourth time unit;

determining an actual geographic region performance value change between the first geographic region performance value and a prior geographic region performance value for the geographic sub-region, wherein determining the actual geographic region performance value change comprises comparing the combined geographic region performance value and the prior geographic region performance value; and identifying a crop health anomaly based on the geographic region performance value change and an expected geographic region performance value change for the geographic sub-region.

10. The method of claim 9, wherein:

determining the actual geographic region performance value change comprises calculating a difference between the first geographic region performance value and the prior geographic region performance value, wherein the first and second geographic region performance values correspond to a first and second calendar month within a current growing season, respectively;

wherein the expected geographic region performance value change is based on a difference between a third geographic region performance value and a fourth geographic region performance value, the third and fourth geographic region performance values corresponding to the first and second calendar month within a historic growing season, respectively;

wherein identifying the crop health anomaly comprises defining the geographic sub-region as an anomalous geographic sub-region of a set of anomalous geographic sub-regions, in response to the actual geographic region performance value change differing beyond a predetermined threshold from an expected geographic region performance value change for the geographic sub-region, and wherein identifying the crop health anomaly comprises identifying the crop health anomaly based on the set of anomalous geographic sub-regions.

11. The method of claim 9, wherein identifying the crop health anomaly comprises:

receiving a supplemental dataset associated with the actual geographic region performance value change, wherein the supplemental dataset comprises at least one of: a soil characteristic, a weather characteristic, and a user input;

comparing the supplemental dataset to a historic supplemental dataset associated with the expected geographic region performance value change, wherein the historic supplemental dataset comprises at least one of: a historic soil characteristic, a historic weather characteristic, and a historic user input; and identifying the crop health anomaly based on comparing the supplemental dataset to the historic supplemental dataset.

12. The method of claim 9, wherein the first, the second, the third, and the fourth time units are within a shared growing season.

13. The method of claim 12, wherein the first and the second time units correspond to a first calendar month within the shared growing season, and wherein the third and the fourth time units correspond to a second calendar month within the shared growing season.

14. The method of claim 9, further comprising:

diagnosing the crop health anomaly; and presenting a diagnosis of the crop health anomaly to a user at a user device.

15. The method of claim 14, wherein diagnosing the crop health anomaly comprises:

identifying anomalous geographic sub-regions with crop health anomalies within the geographic region;

selecting an anomaly diagnosis based on a pattern of anomalous geographic sub-regions with crop health anomalies within the geographic region.

16. The method of claim 9, further comprising, in response to identifying the crop health anomaly:
   determining a crop treatment based on the crop health anomaly; and
   presenting the crop treatment for the geographic sub-region to a user at a user device.

17. The method of claim 9, wherein generating the first geographic region performance value comprises:
   generating a vegetative performance value for the first image element;
   mapping the first image element to a crop type, wherein the first image element is one of a subset of the set of image elements, and wherein the subset of image elements is mapped to the crop type;
   determining a percentile ranking of the vegetative performance value relative to remaining vegetative performance values associated with the subset of image elements; and
   generating the first geographic region performance value based on the percentile ranking.

18. A method for monitoring crop health of a geographic region, the method comprising:
   receiving a first image comprising a set of image elements, the first image corresponding to a first time unit;
   mapping a first image element of the set of image elements to a geographic sub-region of the geographic region;
   determining a first geographic region performance value for the geographic sub-region based on the first image element;
   determining an actual geographic region performance value change between the first geographic region performance value and a prior geographic region performance value for the geographic sub-region, wherein determining the actual geographic region performance value change comprises calculating a difference between the first geographic region performance value and the prior geographic region performance value, wherein the first and second geographic region performance values correspond to a first and second calendar month within a current growing season, respectively; and
   identifying a crop health anomaly based on the geographic region performance value change and an expected geographic region performance value change for the geographic sub-region, wherein the expected geographic region performance value change is based on a difference between a third geographic region performance value and a fourth geographic region performance value, the third and fourth geographic region performance values corresponding to the first and second calendar month within a historic growing season, respectively, wherein identifying the crop health anomaly comprises defining the geographic sub-region as an anomalous geographic sub-region of a set of anomalous geographic sub-regions, in response to the actual geographic region performance value change differing beyond a predetermined threshold from an expected geographic region performance value change for the geographic sub-region, and wherein identifying the crop health anomaly comprises identifying the crop health anomaly based on the set of anomalous geographic sub-regions.

19. The method of claim 18, wherein identifying the crop health anomaly comprises:
   receiving a supplemental dataset associated with the actual geographic region performance value change, wherein the supplemental dataset comprises at least one of: a soil characteristic, a weather characteristic, and a user input;
   comparing the supplemental dataset to a historic supplemental dataset associated with the expected geographic region performance value change, wherein the historic supplemental dataset comprises at least one of: a historic soil characteristic, a historic weather characteristic, and a historic user input; and
   identifying the crop health anomaly based on comparing the supplemental dataset to the historic supplemental dataset.

20. The method of claim 18, further comprising, in response to identifying the crop health anomaly:
   determining a crop treatment based on the crop health anomaly; and
   presenting the crop treatment for the geographic sub-region to a user at a user device.

* * * * *